(12) United States Patent
Hu et al.

(10) Patent No.: US 9,988,637 B2
(45) Date of Patent: Jun. 5, 2018

(54) **CAS9 PLASMID, GENOME EDITING SYSTEM AND METHOD OF *ESCHERICHIA COLI***

(71) Applicants: NATIONAL TSING HUA UNIVERSITY, Hsinchu (TW); CHANG CHUN PLASTICS CO., LTD, Taipei (TW); CHANG CHUN PETROCHEMICAL CO., LTD, Taipei (TW)

(72) Inventors: Yu Chen Hu, Hsinchu (TW); Mu-En Chung, Hsinchu (TW); I-Hsin Yeh, Yunlin County (TW); Hung Li, Hsinchu (TW); Li-Yu Sung, Taoyuan (TW)

(73) Assignees: NATIONAL TSING HUA UNIVERISTY, Hsinchu (TW); CHANG CHUN PLASTICS CO., LTD, Taipei (TW); CHANG CHUN PETROCHEMICAL CO., LTD, Taipei (TW)

( * ) Notice: Subject to any disclaimer, the term of this patent is extended or adjusted under 35 U.S.C. 154(b) by 0 days. days.

(21) Appl. No.: 15/495,580

(22) Filed: Apr. 24, 2017

(65) Prior Publication Data

US 2017/0226522 A1    Aug. 10, 2017

Related U.S. Application Data

(63) Continuation-in-part of application No. 15/066,063, filed on Mar. 10, 2016.

(51) Int. Cl.
| | |
|---|---|
| *C12N 15/73* | (2006.01) |
| *C12N 9/22* | (2006.01) |
| *C12N 15/11* | (2006.01) |
| *C12N 15/72* | (2006.01) |
| *C12N 15/90* | (2006.01) |
| *C07K 14/245* | (2006.01) |

(52) U.S. Cl.
CPC ............ *C12N 15/73* (2013.01); *C07K 14/245* (2013.01); *C12N 9/22* (2013.01); *C12N 15/11* (2013.01); *C12N 15/72* (2013.01); *C12N 15/902* (2013.01); *C12Y 301/11003* (2013.01); *C12N 2310/20* (2017.05); *C12N 2800/101* (2013.01); *C12N 2830/006* (2013.01)

(58) Field of Classification Search
None
See application file for complete search history.

*Primary Examiner* — Mindy G Brown
(74) *Attorney, Agent, or Firm* — Li & Cai Intellectual Property (USA) Office

(57) ABSTRACT

A Cas9 expression plasmid, a genome editing system and a genome editing method for *Escherichia coli* are provided. The Cas9 expression plasmid includes a tracrRNA sequence, a Cas9 gene and a chloramphenicol resistance gene ($Cm^R$). The Cas9 expression plasmid is applied to CRISPR/Cas-coupled λ-red recombineering system for editing genomes of *E. coli* with high efficiency.

16 Claims, 11 Drawing Sheets

Linear DNA purified without dialysis

Linear DNA purified with dialysis

SEQUENCE LISTING

<160> NUMBER OF SEQ ID NOS: 11

<210> SEQ ID NO 1
<211> LENGTH: 8618
<212> TYPE: DNA
<213> ORGANISM: Artificial Sequence
<220> FEATURE:
<223> OTHER INFORMATION: pCas9'

<400> SEQUENCE: 1

```
tcgaccgatg cccttgagag ccttcaaccc agtcagctcc ttccggtggg cgcggggcat      60
gactatcgtc gccgcactta tgactgtctt ctttatcatg caactcgtag acaggtgcc      120 ggcagcgctc tgggtcattt tcggcgagga ccgctttcgc tggagcgcga cgatgatcgg      180
cctgtcgctt gcggtattcg gaatcttgca cgccctcgct caagccttcg tcactggtcc      240
cgccaccaaa cgtttcggcg agaagcaggc cattatcgcc ggcatggcgg ccgacgcgct      300
gggctacgtc ttgctggcgt tcgcgacgcg aggctggatg gccttcccca ttatgattct      360
tctcgcttcc ggcggcatcg ggatgcccgc gttgcaggcc atgctgtcca ggcaggtaga      420
tgacgaccat cagggacagc ttcaaggatc gctcgcggct cttaccagcc taacttcgat      480
cattggaccg ctgatcgtca cggcgattta tgccgcctcg gcgagcacat ggaacgggtt      540
ggcatggatt gtaggcgccg ccctatacct tgtctgcctc cccgcgttgc gtcgcggtgc      600
atggagccgg gccacctcga cctgaatgga agccggcggc acctcgctaa cggattcacc      660
actccaagaa ttggagccaa tcaattcttg cggagaactg tgaatgcgca aaccaaccct      720
tggcagaaca tatccatcgc gtccgccatc tccagcagcc gcacgcggcg catctcgggc      780
agcgttgggt cctggccacg ggtgcgcatg atcgtgctct tgtcgttgag gacccggcta      840
ggctggcggg gttgccttac tggttagcag aatgaatcac cgatacgcga gcgaacgtga      900
agcgactgct gctgcaaaac gtctgcgacc tgagcaacaa catgaatggt cttcggtttc      960
cgtgtttcgt aaagtctgga aacgcggaag tcccctacgt gctgctgaag ttgcccgcaa     1020
cagagagtgg aaccaaccgg tgataccacg atactatgac tgagagtcaa cgccatgagc     1080
ggcctcattt cttattctga gttacaacag tccgcaccgc tgtccggtag ctccttccgg     1140
```

```
tgggcgcggg gcatgactat cgtcgccgca cttatgactg tcttctttat catgcaactc      1200
gtaggacagg tgccggcagc gcccaacagt cccccggcca cggggcctgc caccataccc      1260
acgccgaaac aagcgccctg caccattatg ttccggatct gcatcgcagg atgctgctgg      1320
ctaccctgtg gaacacctac atctgtatta acgaagcgct aaccgttttt atcaggctct      1380
gggaggcaga ataaatgatc atatcgtcaa ttattacctc cacggggaga gcctgagcaa      1440
actggcctca ggcatttgag aagcacacgt cacactgct tccggtagtc aataaaccgg       1500
taaaccagca atagacataa gcggctattt aacgaccctg ccctgaaccg acgaccgggt      1560
cgaatttgct ttcgaatttc tgccattcat ccgcttatta tcacttattc aggcgtagca      1620
ccaggcgttt aagggcacca ataactgcct taaaaaaatt acgccccgcc ctgccactca      1680
tcgcagtact gttgtaattc attaagcatt ctgccgacat ggaagccatc acagacggca      1740
tgatgaacct gaatcgccag cggcatcagc accttgtcgc cttgcgtata atatttgccc      1800
atggtgaaaa cggggcgaa gaagttgtcc atattggcca cgtttaaatc aaaactggtg       1860
aaactcaccc agggattggc tgagacgaaa acatattct caataaaccc tttagggaaa       1920
taggccaggt tttcaccgta acacgccaca tcttgcgaat atatgtgtag aaactgccgg      1980
aaatcgtcgt ggtattcact ccagagcgat gaaaacgttt cagtttgctc atggaaaacg      2040
gtgtaacaag ggtgaacact atcccatatc accagctcac cgtctttcat tgccatacgg      2100
aattccggat gagcattcat caggcgggca agaatgtgaa taaggccgg ataaaacttg       2160 tgcttatttt tctttacggt ctttaaaaag gccgtaatat ccagctgaac ggtctggtta      2220
taggtacatt gagcaactga ctgaaatgcc tcaaaatgtt ctttacgatg ccattgggat      2280
atatcaacgg tggtatatcc agtgattttt ttctccattt tagcttcctt agctcctgaa      2340
aatctcgata actcaaaaaa tacgcccggt agtgatctta tttcattatg gtgaaagttg      2400
gaacctctta cgtgccgatc aacgtctcat tttcgccaaa agttggccca gggcttcccg      2460
gtatcaacag ggacaccagg atttatttat tctgcgaagt gatcttccgt cacaggtatt      2520
tattcggcgc aaagtgcgtc gggtgatgct gccaacttac tgatttagtg tatgatggtg      2580
tttttgaggt gctccagtgg cttctgtttc tatcagctgt ccctcctgtt cagctactga      2640
cggggtggtg cgtaacggca aaagcaccgc cggacatcag cgctagcgga gtgtatactg      2700
gcttactatg ttggcactga tgagggtgtc agtgaagtgc ttcatgtggc aggagaaaaa      2760
aggctgcacc ggtgcgtcag cagaatatgt gatacaggat atattccgct tcctcgctca      2820
ctgactcgct acgctcggtc gttcgactgc ggcgagcgga aatggcttac gaacggggcg      2880
gagatttcct ggaagatgcc aggaagatac ttaacaggga agtgagaggg ccgcggcaaa      2940 gccgttttc cataggctcc gccccctga caagcatcac gaaatctgac gctcaaatca       3000
gtggtggcga aacccgacag gactataaag ataccaggcg tttccccctg gcggctccct      3060
cgtgcgctct cctgttcctg cctttcggtt taccggtgtc attccgctgt tatggccgcg      3120
tttgtctcat tccacgcctg acactcagtt ccgggtaggc agttcgctcc aagctggact      3180
gtatgcacga accccccgtt cagtccgacc gctgcgcctt atccggtaac tatcgtcttg      3240
agtccaaccc ggaaagacat gcaaaagcac cactggcagc agccactggt aattgattta      3300
gaggagttag tcttgaagtc atgcgccggt taaggctaaa ctgaaaggac aagttttggt      3360
gactgcgctc ctccaagcca gttacctcgg ttcaaagagt tggtagctca gagaaccttc      3420
gaaaaaccgc cctgcaaggc ggttttttcg ttttcagagc aagagattac gcgcagacca      3480
aaacgatctc aagaagatca tcttattaat cagataaaat atttctagat ttcagtgcaa      3540
```

```
tttatctctt caaatgtagc acctgaagtc agccccatac gatataagtt gtaattctca    3600
tgtttgacag cttatcatcg ataagcttta atgcggtagt ttatcacagt taaattgcta    3660
acgcagtcag gcaccgtgta tgaaatctaa caatgcgctc atcgtcatcc tcggcaccgt    3720
caccctggat gctgtaggca taggcttggt tatgccggta ctgccgggcc tcttgcggga    3780
ttacgaaatc atcctgtgga gcttagtagg tttagcaaga tggcagcgcc taaatgtaga    3840
atgataaaag gattaagaga ttaatttccc taaaaatgat aaaacaagcg ttttgaaagc    3900
gcttgttttt ttggtttgca gtcagagtag aatagaagta tcaaaaaaag caccgactcg    3960
gtgccacttt ttcaagttga taacggacta gccttatttt aacttgctat gctgttttga    4020
atggttccaa caagattatt ttataacttt tataacaaat aatcaaggag aaattcaaag    4080
aaatttatca gccataaaac aatacttaat actatagaat gataacaaaa taaactactt    4140
tttaaaagaa ttttgtgtta taatctattt attattaagt attgggtaat atttttttgaa    4200 gagatatttt gaaaaagaaa aattaaagca tattaaacta atttcggagg tcattaaaac    4260
tattattgaa atcatcaaac tcattatgga tttaatttaa acttttatt ttaggaggca    4320 aaaatggata agaaatactc aataggctta gatatcggca caaatagcgt cggatgggcg    4380
gtgatcactg atgaatataa ggttccgtct aaaaagttca aggttctggg aaatacagac    4440
cgccacagta tcaaaaaaaa tcttataggg gctcttttat ttgacagtgg agagacagcg    4500
gaagcgactc gtctcaaacg gacagctcgt agaaggtata cacgtcggaa gaatcgtatt    4560
tgttatctac aggagatttt ttcaaatgag atggcgaaag tagatgatag tttctttcat    4620
cgacttgaag agtctttttt ggtggaagaa gacaagaagc atgaacgtca tcctattttt    4680
ggaaatatag tagatgaagt tgcttatcat gagaaatatc caactatcta tcatctgcga    4740
aaaaaattgg tagattctac tgataaagcg gatttgcgct taatctattt ggccttagcg    4800
catatgatta agtttcgtgg tcattttttg attgagggag atttaaatcc tgataatagt    4860
gatgtggaca aactatttat ccagttggta caaacctaca atcaattatt tgaagaaaac    4920
cctattaacg caagtggagt agatgctaaa gcgattcttt ctgcacgatt gagtaaatca    4980
agacgattag aaaatctcat tgctcagctc cccggtgaga agaaaaatgg cttatttggg    5040
aatctcattg ctttgtcatt gggtttgacc cctaatttta aatcaaattt tgatttggca    5100
gaagatgcta aattacagct ttcaaaagat acttacgatg atgatttaga taatttattg    5160
gcgcaaattg gagatcaata tgctgatttg ttttggcag ctaagaattt atcagatgct    5220
atttttactt cagatatcct aagagtaaat actgaaataa ctaaggctcc cctatcagct    5280
tcaatgatta aacgctacga tgaacatcat caagacttga ctcttttaaa gctttagtt    5340 cgacaacaac ttccagaaaa gtataaagaa atcttttttg atcaatcaaa aacggatat    5400 gcaggttata ttgatggggg agctagccaa gaagaatttt ataaatttat caaaccaatt    5460
ttagaaaaaa tggatggtac tgaggaatta ttggtgaaac taaatcgtga agatttgctg    5520
cgcaagcaac ggacctttga caacggctct attccccatc aaattcactt gggtgagctg    5580
catgctattt tgagaagaca agaagacttt tatccatttt taaagacaa tcgtgagaag    5640 attgaaaaaa tcttgacttt tcgaattcct tattatgttg gtccattggc gcgtggcaat    5700
agtcgttttg catggatgac tcggaagtct gaagaaacaa ttaccccatg gaattttgaa    5760
gaagttgtcg ataaaggtgc ttcagctcaa tcatttattg aacgcatgac aaactttgat    5820
aaaaatcttc caaatgaaaa agtactacca aaacatagtt tgctttatga gtattttacg    5880
```

```
gtttataacg aattgacaaa ggtcaaatat gttactgaag gaatgcgaaa accagcattt    5940
ctttcaggtg aacagaagaa agccattgtt gatttactct tcaaaacaaa tcgaaaagta    6000
accgttaagc aattaaaaga agattatttc aaaaaaatag aatgttttga tagtgttgaa    6060
atttcaggag ttgaagatag atttaatgct tcattaggta cctaccatga tttgctaaaa    6120
attattaaag ataaagattt tttggataat gaagaaaatg aagatatctt agaggatatt    6180
gttttaacat tgaccttatt tgaagatagg gagatgattg aggaaagact aaaacatat     6240 gctcacctct ttgatgataa ggtgatgaaa cagcttaaac gtcgccgtta tactggttgg    6300
ggacgtttgt ctcgaaaatt gattaatggt attagggata agcaatctgg caaaacaata    6360 ttagatttt tgaaatcaga tggttttgcc aatcgcaatt ttatgcagct gatccatgat    6420
gatagtttga catttaaaga agacattcaa aaagcacaag tgtctggaca aggcgatagt    6480
ttacatgaac atattgcaaa tttagctggt agccctgcta ttaaaaaagg tattttacag    6540
actgtaaaag ttgttgatga attggtcaaa gtaatggggc ggcataagcc agaaaatatc    6600
gttattgaaa tggcacgtga aaatcagaca actcaaaagg gccagaaaaa ttcgcgagag    6660
cgtatgaaac gaatcgaaga aggtatcaaa gaattaggaa gtcagattct taaagagcat    6720
cctgttgaaa atactcaatt gcaaaatgaa aagctctatc tctattatct ccaaaatgga    6780
agagacatgt atgtggacca agaattagat attaatcgtt taagtgatta tgatgtcgat    6840
cacattgttc cacaaagttt ccttaaagac gattcaatag acaataaggt cttaacgcgt    6900
tctgataaaa tcgtggtaa atcggataac gttccaagtg aagaagtagt caaaaagatg    6960
aaaaactatt ggagacaact tctaaacgcc aagttaatca ctcaacgtaa gtttgataat    7020
ttaacgaaag ctgaacgtgg aggtttgagt gaacttgata agctggtttt tatcaaacgc    7080
caattggttg aaaactcgcca atcactaag catgtggcac aaattttgga tagtcgcatg    7140
aatactaaat acgatgaaaa tgataaactt attcgagagg ttaaagtgat taccttaaaa    7200
tctaaattag tttctgactt ccgaaaagat ttccaattct ataaagtacg tgagattaac    7260
aattaccatc atgcccatga tgcgtatcta aatgccgtcg ttggaactgc tttgattaag    7320
aaatatccaa aacttgaatc ggagtttgtc tatggtgatt ataaagttta tgatgttcgt    7380
aaaatgattg ctaagtctga gcaagaaata ggcaaagcaa ccgcaaaata tttcttttac    7440
tctaatatca tgaacttctt caaaacagaa attacacttg caaatggaga gattcgcaaa    7500
cgccctctaa tcgaaactaa tggggaaact ggagaaattg tctgggataa agggcgagat    7560
tttgccacag tgcgcaaagt attgtccatg ccccaagtca atattgtcaa gaaaacagaa    7620
gtacagacag gcggattctc caaggagtca attttaccaa aaagaaattc ggacaagctt    7680
attgctcgta aaaagactg ggatccaaaa aaatatggtg gttttgatag tccaacggta    7740
gcttattcag tcctagtggt tgctaaggtg gaaaaaggga atcgaagaa gttaaaatcc    7800 gttaaagagt tactagggat cacaattatg gaaagaagtt cctttgaaaa aaatccgatt    7860
gactttttag aagctaaagg atataaggaa gttaaaaaag acttaatcat taaactacct    7920
aaatatagtc ttttttgagtt agaaaacggt cgtaaacgga tgctggctag tgccggagaa    7980
ttacaaaaag gaaatgagct ggctctgcca agcaaatatg tgaattttt atatttagct    8040 agtcattatg aaaagttgaa gggtagtcca gaagataacg aacaaaaaca attgtttgtg    8100
gagcagcata agcattattt agatgagatt ttgagcaaa tcagtgaatt ttctaagcgt    8160 gttatttag cagatgccaa tttagataaa gttcttagtg catataacaa acatagagac    8220
aaaccaatac gtgaacaagc agaaaatatt attcatttat ttacgttgac gaatcttgga    8280
```

```
gctcccgctg cttttaaata ttttgataca acaattgatc gtaaacgata tacgtctaca    8340
aaagaagttt tagatgccac tcttatccat caatccatca ctggtcttta tgaaacacgc    8400
attgatttga gtcagctagg aggtgactga agtatatttt agatgaagat tatttcttaa    8460
taactaaaaa tatggtataa tactcttaat aaatgcagta atacaggggc ttttcaagac    8520
tgaagtctag ctgagacaaa tagtgcgatt acgaaatttt ttagacaaaa atagtctacg    8580
aggttttaga gctatgctgt tttgaatggt cccaaaac                            8618
```

<210> SEQ ID NO 2
<211> LENGTH: 30
<212> TYPE: DNA
<213> ORGANISM: Artificial Sequence
<220> FEATURE:
<223> OTHER INFORMATION: Spacer sequence of pCRISPR::LacZ

<400> SEQUENCE: 2

```
agatgtgcgg cgagttgcgt gactacctac                                     30
```

<210> SEQ ID NO 3
<211> LENGTH: 20
<212> TYPE: DNA
<213> ORGANISM: Artificial Sequence
<220> FEATURE:
<223> OTHER INFORMATION: Spacer sequence of pCRISPR::gltA

<400> SEQUENCE: 3

```
tcggcatttt cgacagcagg                                                20
```

<210> SEQ ID NO 4
<211> LENGTH: 21
<212> TYPE: DNA
<213> ORGANISM: Artificial Sequence
<220> FEATURE:
<223> OTHER INFORMATION: Spacer sequence of pCRISPR::lpdA

<400> SEQUENCE: 4

```
gacctaaatc agcgcaacgg a                                              21
```

<210> SEQ ID NO 5
<211> LENGTH: 68
<212> TYPE: DNA
<213> ORGANISM: Artificial Sequence
<220> FEATURE:
<223> OTHER INFORMATION: Amplified linear DNA forward primer

<400> SEQUENCE: 5

```
gctcgtatgt tgtgtggaat tgtgagcgga taacaatttc acacaggaaa catcaggtcg    60
aggtggcc                                                             68
```

<210> SEQ ID NO 6
<211> LENGTH: 71
<212> TYPE: DNA
<213> ORGANISM: Artificial Sequence
<220> FEATURE:
<223> OTHER INFORMATION: Amplifeid linear DNA reverse primer-1

<400> SEQUENCE: 6

```
tttgatggac catttcggca cagccgggaa gggctggtct tcatccacgc gctttcgcgg    60
gatcgagatc t                                                         71
```

<210> SEQ ID NO 7

```
<210> SEQ ID NO 7
<211> LENGTH: 74
<212> TYPE: DNA
<213> ORGANISM: Artificial Sequence
<220> FEATURE:
<223> OTHER INFORMATION: Amplified linear DNA reverse primer-2

<400> SEQUENCE: 7
tttgatggac catttcggca cagccgggaa gggctggtct tcatccacgc gccggatata      60
gttcctcctt tcag                                                       74

<210> SEQ ID NO 8
<211> LENGTH: 60
<212> TYPE: DNA
<213> ORGANISM: Artificial Sequence
<220> FEATURE:
<223> OTHER INFORMATION: amplified linear DNA reverse primer-3

<400> SEQUENCE: 8
tttgatggac catttcggca cagccgggaa gggctggtct tcatccacgc gggtctgaca      60

<210> SEQ ID NO 9
<211> LENGTH: 83
<212> TYPE: DNA
<213> ORGANISM: Artificial Sequence
<220> FEATURE:
<223> OTHER INFORMATION: Linear donor DNA

<400> SEQUENCE: 9
ggatgttaac aatcctcgtc atcgtgaaat tgccgcgttc ctgcagctgt cgaaaatgcc      60
gaccatggcc gcgatgtgtt aca                                             83

<210> SEQ ID NO 10
<211> LENGTH: 3014
<212> TYPE: DNA
<213> ORGANISM: Artificial Sequence
<220> FEATURE:
<223> OTHER INFORMATION: Donor DNA of lpdA gene

<400> SEQUENCE: 10
cctgaaagac gacgggtatg accgccggag ataaatatat agaggtcatg atgagtactg      60
aaatcaaaac tcaggtcgtg gtacttgggg caggccccgc aggttactct gcagccttcc     120
gttgcgctga tttaggtctg gaaaccgtca tcgtagaacg ttacagcacc ctcggtggtg     180
tttgtctgaa cgtgggttgt atcccttcta aagcgctgct gcacgtggca aaagttatcg     240
aagaagcgaa agcgctggcc gaacacggca tcgtttttcgg cgaaccgaaa actgacattg     300
acaagatccg cacctggaaa gaaaaagtca tcactcagct gaccggtggt ctggctggca     360
tggccaaagg tcgtaaagtg aaggtggtta acggtctggg taaatttacc ggcgctaaca     420
ccctggaagt ggaaggcgaa aacggcaaaa ccgtgatcaa cttcgacaac gccatcatcg     480
cggcgggttc ccgtccgatt cagctgccgt ttatcccgca tgaagatccg cgcgtatggg     540
actccaccga cgcgctggaa ctgaaatctg taccgaaacg catgctggtg atgggcggcg     600
gtatcatcgg tctggaaatg ggtaccgtat accatgcgct gggttcagag attgacgtgg     660
tggaaatgtt cgaccaggtt atcccggctg ccgacaaaga cgtggtgaaa gtcttccacca     720 aacgcatcag caagaaattt aacctgatgc tggaaaccaa agtgactgcc gttgaagcga     780 agaagacgg tatttacgtt tccatggaag taaaaaagc accggcggaa gcgcagcgtt     840
acgacgcagt gctggtcgct atcggccgcg taccgaatgg taaaaacctc gatgcaggta     900 agctggcgt ggaagttgac gatcgcggct tcatccgcgt tgacaaacaa atgcgcacca     960
```

```
acgtgccgca catctttgct atcggcgata tcgtcggtca gccgatgctg gcgcacaaag    1020
gtgtccatga aggccacgtt gccgcagaag ttatctccgg tctgaaacac tacttcgatc    1080
cgaaagtgat cccatccatc gcctacacta aaccagaagt ggcatgggtc ggtctgaccg    1140
agaaagaagc gaaagagaaa ggcatcagct acgaaaccgc caccttcccg tgggctgctt    1200
ccggccgtgc tatcgcttct gactgcgcag atggtatgac caaactgatc ttcgacaaag    1260
agacccaccg tgttatcggc ggcgcgattg tcggcaccaa cggcggcgag ctgctgggtg    1320
agatcggcct ggctatcgag atgggctgtg acgctgaaga catcgccctg accatccacg    1380
ctcacccgac tctgcacgag tccgttggcc tggcggcgga agtgttcgaa ggcagcatca    1440
ccgacctgcc aaacgccaaa gcgaagaaaa agtaaaagct tggaattcgc ccgggacaag    1500
cttgtcgaga ctgcaggaag ttcctatact ttctagagaa taggaacttc gcggccgctc    1560
aggtcgaggt ggcccggctc catgcaccgc gacgcaacgc ggggaggcag acaaggtata    1620
gggcggcgcc tacaatccat gccaacccgt tccatgtgct cgccgaggcg cataaatcg    1680 ccgtgacgat cagcggtcca gtgatcgaag ttaggctggt aagagccgcg agcgatcctt    1740
gaagctgtcc ctgatggtcg tcatctacct gcctggacag catggcctgc aacgcgggca    1800
tcccgatgcc gccggaagcg agaagaatca taatggggaa ggccatccag cctcgcgtcg    1860
cgaacgccag caagacgtag cccagcgcgt cggccgccat gccggcgata atggcctgct    1920
tctcgccgaa acgtttggtg gcgggaccag tgacgaaggc ttgagcgagg gcgtgcaaga    1980
ttccgaatac cgcaagcgac aggccgatca tcgtcgcgct ccagcgaaag cggtcctcgc    2040
cgaaaatgac ccagagcgct gccggcacct gtcctacgag ttgcatgata aagaagacag    2100
tcataagtgc ggcgacgata gtcatgcccc gcgcccaccg gaaggagctg actgggttga    2160
aggctctcaa gggcatcggt cgacgctctc ccttatgcga ctcctgcatt aggaagcagc    2220
ccagtagtag gttgaggccg ttgagcaccg ccgccgcaag gaatggtgca tgcaaggaga    2280
tggcgcccaa cagtccccg gccacggggc ctgccaccat acccacgccg aaacaagcgc    2340
tcatgagccc gaagtggcga gcccgatctt ccccatcggt gatgtcggcg atataggcgc    2400
cagcaaccgc acctgtggcg ccggtgatgc cggccacgat gcgtccggcg tagaggatcc    2460
acaggacggg tgtggtcgcc atgatcgcgt agtcgatagt ggctccaagt agcgaagcga    2520
gcaggactgg gcggcggcca aagcggtcgg acagtgctcc gagaacgggt gcgcatagaa    2580
attgcatcaa cgcatatagc gctagcagca cgccatagtg actggcgatg ctgtcggaat    2640
ggacgatatc ccgcaagagg cccggcagta ccggcataac caagcctatg cctacagcat    2700
ccagggtgac ggtgccgagg atgacgatga gcgcattgtt agatttcata cacggtgcct    2760
gactgcgtta gcaatttaac tgtgataaac taccgcatta agcttatcg atgataagct    2820 gtcaaacagg cctttgaatt ccgcgcgctt cggaccggga tcgggatctc gagccatggt    2880
gctagcgaag ttcctatact ttctagagaa taggaacttc gcatgcgta ccgggagatg    2940 ggggaggcta actgaaacac ggagttgttc gtttgccgga acatccggca attaaaaaag    3000
cggctaacca cgcc                                                     3014
```

```
<210> SEQ ID NO 11
<211> LENGTH: 35
<212> TYPE: DNA
<213> ORGANISM: Escherichia coli

<400> SEQUENCE: 11
ccgcgttcct gcagctgtcg aaaatgccga ccatg                              35
```

CAS9 PLASMID, GENOME EDITING SYSTEM AND METHOD OF ESCHERICHIA COLI

CROSS REFERENCE TO RELATED APPLICATION

This application is a continuation-in-part of U.S. application Ser. No. 15/066,063, filed on 10 Mar. 2016 and entitled "Method for bacterial genome editing", now pending, the entire disclosures of which are incorporated herein by reference.

BACKGROUND

1. Technical Field

The present disclosure relates to a genome editing system and a method thereof for microorganisms, and in particular, to a genome editing system and a method thereof for chromosomal integration/deletion/replacement in Escherichia coli (E. coli).

2. Description of Related Art

Metabolic engineering plays a crucial role for bio-based production of fuels, chemicals, and materials from renewable biomass, and often involves integration of multiple genes to re-direct metabolic fluxes. Hence, chromosomal integration and/or replacement of large DNA into microorganisms remains an important issue in bioengineering.

The most widely used genome editing tools for chromosomal integration/replacement in Escherichia coli may be the endogenous RecA-dependent homologous recombination system, which, however, is inefficient and requires long (about 1,000 bp) flanking regions homologous to the sequence of the desired insertion site (homology arm). Recombineering requires only a pair of short (40-50 bp) homology arms, but the integration efficiency drops sharply for DNA fragments >1,500 bp, and integration of fragments >2,500 bp using 50 bp homology arms is very difficult.

Recently, an RNA-guided editing system based on CRISPR/Cas9-mediated DNA cleavage was developed for programmable, customizable genome engineering. Compared to the conventional genome editing technique, CRISPR/Cas9 can be used to knockout or insert several genes at the same time, and the genome editing technique of the CRISPR/Cas9 is relatively easier than the conventional genome editing technique, so that convenience of genome editing is increased.

Although ensuing reports have demonstrated gene insertion, deletion, and replacement using the CRISPR/Cas9 system, integration of large DNA into E. coli chromosome remains difficult and inefficiency. More specifically, the integration efficiency drops sharply to 35% once DNA fragments are increased to be longer than 5 kb.

Therefore, there is still room for improvement in the efficiency of genome editing by CRISPR/Cas9 system in bacteria and in the future bioengineering applications thereof.

SUMMARY

The object of the present disclosure is to provide a genome editing system and a method for microorganisms to elevate the homologous recombineering efficiency.

In order to achieve the aforementioned object, according to one embodiment of the present disclosure, a Cas9 expression plasmid is provided. The Cas9 expression plasmid includes a nucleotide sequence of SEQ ID NO: 1 harboring a tracrRNA sequence, a Cas9 gene sequence and a chloramphenicol resistance gene ($Cm^R$) sequence.

In order to achieve the aforementioned object, according to one embodiment of the present disclosure, a genome editing system for Escherichia coli (E. coli) is provided. The genome editing system for E. coli including: an E. coli strain; a Cas9 expression plasmid, a λ-red recombinase expression plasmid, a crRNA expression plasmid and a linear DNA. The λ-red recombinase expression plasmid includes a $P_{araB}$ promoter, a Gam gene, a Bet gene and an Exo gene sequentially. The crRNA expression plasmid includes a promoter sequence, a crRNA sequence and a spacer sequence. The spacer sequence is complementary to a first specific sequence on a chromosome of the E. coli strain. The linear DNA includes a right homology arm (HRR), a donor DNA and a left homology arm (HRL). The right homology arm (HRR) and the left homology arm (HRL) cooperatively form a homologous recombination region of which the sequence is complementary to a second specific sequence on the chromosome of the E. coli strain.

In order to achieve the aforementioned object, according to another embodiment of the present disclosure, a genome editing method for Escherichia coli is provided.

The genome editing method for E. coli includes the following steps. Firstly, provide an E. coli strain. Secondly, constructing a Cas9 expression plasmid having a nucleotide sequence of SEQ ID NO: 1, in which the Cas9 expression plasmid includes a tracrRNA sequence, Cas9 gene sequence and a chloramphenicol resistance gene (CmR) sequence. Afterwards, constructing a λ-red recombinase expression plasmid sequentially harboring a $P_{araB}$ promoter, a Gam gene, a Bet gene and an Exo gene. Then, constructing a crRNA expression plasmid harboring a promoter sequence, a crRNA sequence and a spacer sequence, in which the spacer sequence is complementary to a first specific sequence on a chromosome of the E. coli strain. Afterwards, preparing a linear DNA including a right homology arm (HRR), a donor DNA and a left homology arm (HRL). The right homology arm and the left homology arm cooperatively form a homologous recombination region of which the sequence is complementary to a second specific sequence on the chromosome of the E. coli strain. The Cas9 expression plasmid and the λ-red recombinase expression plasmid are then co-transformed into the E. coli strain to produce a first transformant. Then, the expression of Gam, Exo, and Beta proteins of the λ-red recombinase expression plasmid are triggered by adding arabinose. Afterwards, the crRNA expression plasmid and the linear DNA are co-transformed into the first transformant to obtain a second tansformant. Finally, the second transformant is incubated, in which the Cas9 expression plasmid expresses a tracrRNA and a Cas9 protein, and the crRNA expression plasmid expresses a crRNA. The tracrRNA, the Cas9 protein and the crRNA cooperatively form a Cas9 protein complex to produce a double-stranded break specific to the first specific sequence of the second transformant. The homologous recombination region and the second specific sequence of the second transformant undergo homologous recombination to insert the donor DNA into the first specific sequence of the second transformant.

To sum up, the present disclosure achieves the high fidelity integration of dsDNA as large fragments into E. coli chromosome, ameliorates the editing efficiency and overcomes the size limit of integration, replacement and site specific deletion for the bacterial genome. Furthermore, according to the present disclosure, the procedures of introducing synthetic metabolic pathway into bacterium is simplified, so as to allow replacement, integration and site-specific mutations of large DNA segments for genome-wide editing. In addition, the costs of production can be decreased.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

The term "CRISPR/Cas" herein refers to clustered regularly interspaced short palindromic repeats (CRISPR) and CRISPR associated proteins (Cas9) system. CRISPR/Cas is an innate immune system in bacteria and archaea. In the type II system derived from *Streptococcus pyogenes*, the CRISPR locus including an array of direct repeats (DRs)-flanking spacer is transcribed into precursor CRISPR RNA (crRNA), which associates with transacting crRNA (tracrRNA) and is processed into mature crRNA/tracrRNA. Acting in concert with the Cas9 nuclease and guided by the spacer sequence, the complex recognizes trinucleotide protospacer-adjacent motif (PAM) and specifically binds to proximal chromosomal complementary sequence (protospacer, 20 bp), after which Cas9 cleaves chromosomal DNA into a double strand break (DSB) within the target DNA in 3~4 nucleotides upstream of the PAM sequence via RuvC-like and HNH nuclease domains of Cas9. The Cas9 HNH nuclease domain cleaves the complementary strand, whereas the Cas9 RuvC-like domain cleaves the noncomplementary strand.

The term "λ-red recombinase expression plasmid" used herein refers to plasmids that express enzymes for the λ-red system that can be used for cloning or genome engineering and is based on homologous recombination. The λ-red recombineering system has three components (proteins): Exo, Beta and Gam. Gam prevents both the endogenous RecBCD and SbcCD nucleases from digesting linear DNA introduced into the *E. coli*. Exo is a 5'→3' dsDNA-dependent exonuclease. Exo will degrade linear dsDNA starting from the 5' end and generate a partially dsDNA duplex with single-stranded 3' overhangs. Beta binds to the single-stranded 3' overhangs created by Exo to protect the ssDNA and promote its annealing to a complementary ssDNA (usually derived from an exogenous linear DNA) target in the cell.

The term "donor DNA" used herein refers to exogenous DNA sequences obtained from the PCR-amplification products with specific primers based on template plasmids. The template plasmids can be derived from pET-21b(+) (commercially available).

The following exemplary embodiment further illustrates how materials and methods of the present disclosure are practiced in order for those skilled in the art to fully utilize and practice the present disclosure without undue interpretation, and should not be construed as restricting the scope of the present disclosure.

Exemplary Embodiment

1. Cas9 Expression Plasmid of the Present Disclosure

The distinct Cas9 expression plasmid used in present disclosure, which is indicated as pCas9', is obtained by modifying the conventional Cas9 expression plasmid (pCas9). More specifically, a sequence (6,515-8,032 bp) of the commercially available pCas9 (Addgene, Cambridge, Mass. #42876) was removed by Eco31I/FspAI, followed by Klenow enzyme treatment and ligation with T4 DNA ligase to yield pCas9'. The sequence of pCas9' of the present disclosure is shown as SEQ ID NO: 1 in Sequence Listing.

Figure 1:
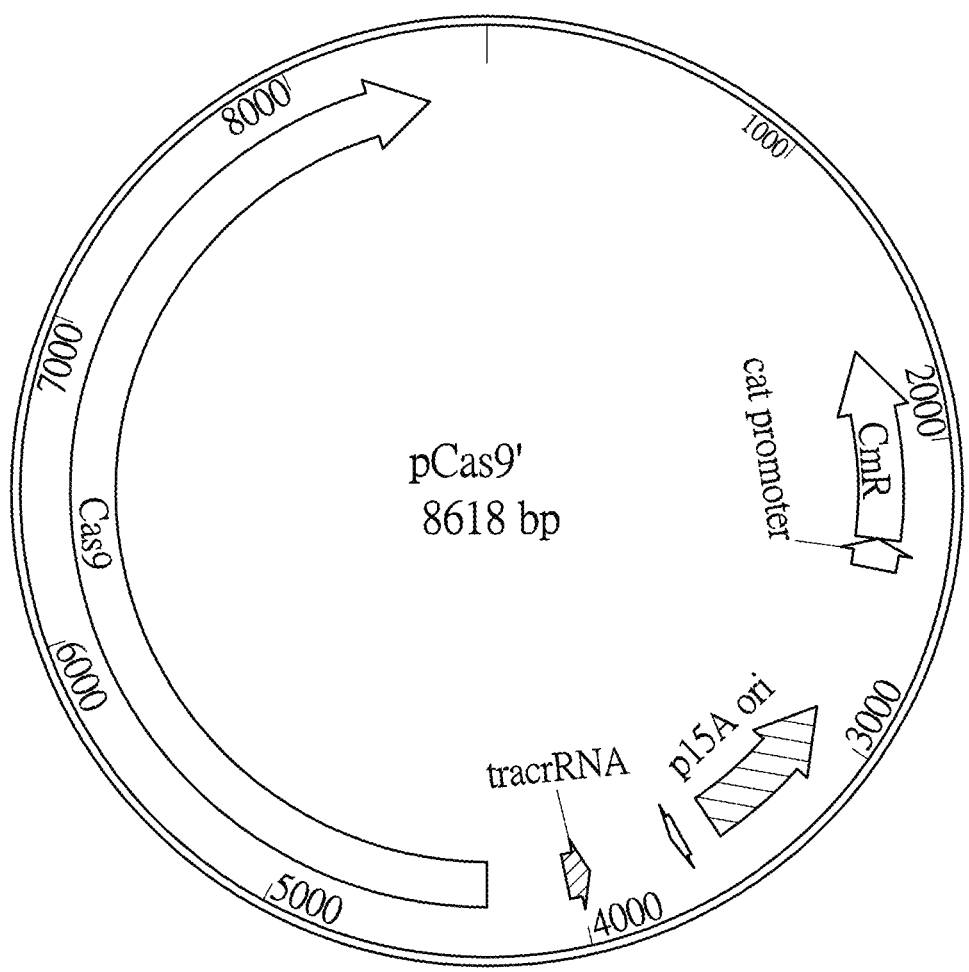
FIG. 1 shows a gene map of the Cas9 expression plasmid (pCas9') according to an embodiment of the present disclosure.

As shown in FIG. 1, the Cas9 expression plasmid of the present disclosure (pCas9') is a low copy number plasmid with the origin of replication (ORI) p15A_origin, and harbors chloramphenicol resistance gene ($Cm^R$), *Streptococcus pyogenes*-derived cas9 gene and tracrRNA sequence driven by respective endogenous promoters.

2. Genome Editing System of *E. coli* of the Present Disclosure

The genome editing system of *E. coli* of the present disclosure includes an *E. coli* strain, a Cas9 expression plasmid-pCas9', a λ-red recombinase expression plasmid, a crRNA expression plasmid and a linear DNA.

The *E. coli* strain used in the present disclosure can be a K-12 strain or a W strain, and preferably, can be selected from the group consisting of MG1655, WΔ5 and WΔ5#1 strains (Food Industrial Development Institute, Hsinchu city, Taiwan).

The Cas9 expression plasmid, pCas9', (as shown in FIG. 1) has a sequence shown as SEQ ID NO: 1 in which contains a sequence of tracrRNA, Cas9 gene and Cm$^R$ gene.

The λ-red recombinase expression plasmid sequentially includes P$_{araB}$, Gam, Bet and Exo genes. According to an embodiment of the present disclosure, the λ-red recombinase expression plasmid is pKD46 (sequence is referred to GenBank: AY048746.1), which harbors the temperature-sensitive oriR101 (with repA101ts for curing at 37° C.), ampicillin resistance gene (Ap$^r$), and the λ-red L-arabinose operon (araC). The λ-red L-arabinose operon (araC) encodes Gam, Bet, and Exo proteins under the control of arabinose-inducible promoter P$_{araB}$.

The crRNA expression plasmid used in the present disclosure includes a promoter sequence, a crRNA sequence and a spacer sequence. The spacer sequence is complementary to a first specific sequence on a chromosome of E. coli. In addition, the crRNA expression plasmid further includes a tracrRNA sequence. The tracrRNA sequence and the spacer sequence cooperatively form a single guide RNA (sgRNA) sequence. The crRNA expression plasmid in a distinct experimental example includes a pCRISPR::LacZ plasmid expressing crRNA specifically targeting LacZ gene of E. coli chromosome, a pCRISPR::gltA plasmid expressing crRNA specifically targeting gltA gene on the chromosome of E. coli and a pCRISPR::lpdA plasmid expressing crRNA specifically targeting lpdA gene on the chromosome of E. coli. The pCRISPR::LacZ plasmid and the pCRISPR::gltA plasmid are constructed by respectively inserting different spacer sequences in pCRISPR::Φ (Addgene #42875) with EcoRI/BamHI, followed by Klenow treatment and T4 DNA ligase ligation. The pCRISPR::Φ harbored kanamycin resistance gene (Km$^R$) and scrambled crRNA (containing two DRs but lacking the spacer targeting any E. coli sequences) were driven by the P$_{LtetO1}$ promoter and ligated into the interspace between two adjacent DRs. The spacer sequence of the pCRISPR::LacZ is shown as SEQ ID NO: 2, and the spacer sequence of the pCRISPR::gltA is shown as SEQ ID NO: 3. The spacer sequence of the pCRISPR::lpdA plasmid is constructed by using the pgRNA-bacteria plasmid which harbors a BBa_J23119 (SpeI) promoter (Addgene #44251) as the donor template. More specifically, the pgRNA-bacteria plasmid is often used for the expression of customizable guide RNA (gRNA) for bacterial gene knockdown. The plasmid pgRNA_lpdA of the present disclosure is constructed by annealing the spacer sequence D354K mutant lpdA (shown as SEQ ID NO: 4) therein so as to harbor the mature sgRNA expression targeting lpdA. Afterwards, the mature sgRNA expression targeting lpdA is digested by EcoRI/BamHI, followed by Klenow treatment and T4 DNA ligase ligation into the pCRISPR::Φ, such that the pCRISPR::lpdA plasmid is constructed.

The linear DNA includes a right homology arm (HRR), a donor DNA and a left homology arm (HRL). The right homology arm and the left homology arm cooperatively forms a homologous recombination region of which the sequence is complementary to a second specific sequence of E. coli. The size of the right homology arm is the same as that of the left homology arm and can be between 40 bp and 80 bp. In addition, the linear DNA can include a first antibiotic resistant gene. The first antibiotic resistant gene can be a tetracycline resistance gene (Tc$^R$, about 1.2 kb). All linear DNA used in the present disclosure were amplified from the plasmids by PCR using about 70 nt primer pairs (referred to Table 1) comprising about 20 nt complementary to the template plasmid, one of which was complementary to Tc$^R$ so that all PCR amplicons were encoded with Tc$^R$. The remaining 50 nt sequence was complementary to the E. coli genome so that the PCR amplicons contains the flanking homology arm for recombination into the genome. To prepare the linear DNA as the editing template, the tetracycline resistance gene together with its endogenous promoter is PCR-amplified from pACYC184 (New England Biolabs) and subcloned into pET-21b(+) (Novagen, Darmstadt, Germany) with BglII to yield pET-21b(+)-Tc. The egfp gene (720 bp) is PCR-amplified from pEGFP-N1 (Clontech, Mountain View, Calif.) and subcloned into pET-21b(+)-Tc with EcoRI/XhoI to yield pET-21b(+)-Tc-EGFP, which is used as the template plasmid for the preparation of 1.4, 2.4, and 3.9 kb linear DNA by PCR. Further, the phaCAB operon (3,851 bp) derived from heterologous Ralstonia eutropha is PCR-amplified from pSY11 and cloned into pET-21b(+) by EcoRI/XhoI to yield pET-21b(+)-phaCAB. A 1,565 bp fragment is digested with XhoI/SalI from pET-21b(+)-phaCAB (2,287-3,851 bp) as a stuffer and subcloned with XhoI/SalI into pET-21b(+)-Tc-EGFP to yield pET-Tc-EG-1565stuf, which is used as the template for PCR-amplification of 5.4 kb linear DNA. Further, a 3,121 bp fragment is PCR-amplified from pET-21b(+)-phaCAB (731-3,851 bp) and subcloned into pET-21b(+)-Tc-EGFP to yield pET-Tc-EG-3121stuf, which is used as the template for PCR-amplification of 7.0 kb linear DNA. Further, two commercial synthetic genes including susD gene (1,356 bp) and 4-hdb gene (1,116 bp) are PCR-amplified and subcloned into pET-Tc-EG-3121stuf to form pET-Tc-EG-3121-SH, which is used as the template for PCR-amplification of 10 kb linear DNA.

TABLE 1

Template plasmids and primers for different linear DNA lengths

| Linear DNA | Template plasmids | Primers |
|---|---|---|
| 1.4 kb | pET-21b(+)-Tc-EGFP | SEQ ID NO: 5<br>SEQ ID NO: 6 |
| 2.4 kb | pET-21b(+)-Tc-EGFP | SEQ ID NO: 5<br>SEQ ID NO: 7 |
| 3.9 kb | pET-21b(+)-Tc-EGFP | SEQ ID NO: 5<br>SEQ ID NO: 8 |
| 5.4 kb | pET-Tc-EG-1565stuff | SEQ ID NO: 5<br>SEQ ID NO: 8 |
| 7.0 kb | pET-Tc-EG-3121stuff | SEQ ID NO: 5<br>SEQ ID NO: 8 |
| 10 kb | pET-Tc-EG-3121-SH | SEQ ID NO: 5<br>SEQ ID NO: 8 |

3. Genome Editing Method of E. coli of the Present Disclosure

Figure 2:
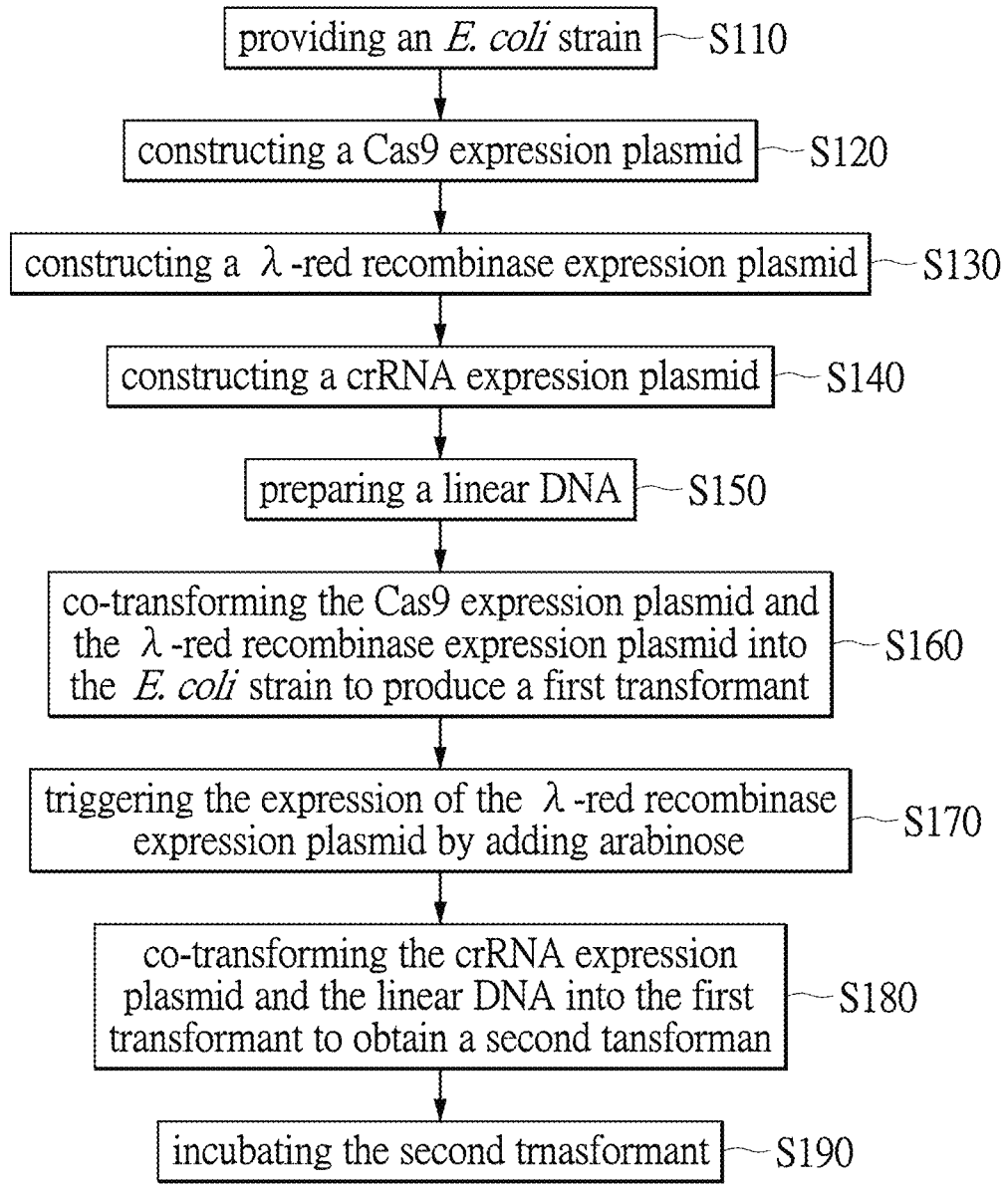
FIG. 2 is a flow chart of a genome editing method of *E. coli* according to the embodiment of the present disclosure.

Referring to FIG. 2 showing a flow chart of a genome editing method 100 of E. coli according to the embodiment of the present disclosure, the genome editing method 100 includes following steps:

Step 110: providing an E. coli strain. The E. coli strain can be a K-12 strain or a W strain, and preferably, can be MG1655, WΔ5 or WΔ5#1 strains.

Step 120: constructing a Cas9 expression plasmid (pCas9'). The sequence of the Cas9 expression plasmid harbors a tracrRNA, Cas9 gene and Cm$^R$ gene.

Step 130: constructing a λ-red recombinase expression plasmid. The λ-red recombinase expression plasmid sequentially harbors $P_{araB}$, Gam, Bet and Exo genes.

Step 140: constructing a crRNA expression plasmid. The crRNA expression plasmid harbors a promoter sequence, a crRNA sequence and a spacer sequence. In addition, the crRNA expression plasmid can further include a tracrRNA sequence. The tracrRNA sequence and the spacer sequence cooperatively form a single guide RNA (sgRNA) sequence.

Step 150: preparing a linear DNA including a right homology arm (HRR), a donor DNA and a left homology arm (HRL). The right homology arm and the left homology arm cooperatively form a homologous recombination region of which the sequence is complementary to a second specific sequence of *E. coli*. The length of the right homology arm and the left homology arm are the same and can be 40 bp to 80 bp. In addition, the linear DNA can include a first antibiotic resistant gene. The first antibiotic resistant gene can be tetracycline resistance gene ($Tc^R$, about 1.2 kb). More specifically, the linear DNA can be prepared by the following protocol. Firstly, providing a template plasmid. Secondly, performing PCR-amplification by a primer pair and obtaining the PCR product, in which the primer pair is composed of a forward primer and a reverse primer. The 5'-end of the forward primer has a sequence of HRL, and the 5'-end of the reverse primer has a sequence that is complementary to the HRR. Afterwards, purifying the PCR product to obtain a DNA solution. Then, eluting the DNA solution to obtain the linear DNA. More specifically, the DNA solution can be eluted through a membrane filter with a pore size of 0.025 μm.

Step 160: co-transforming the Cas9 expression plasmid and the λ-red recombinase expression plasmid into the *E. coli* strain to produce a first transformant. The co-transforming step can be performed by electroporation or other conventional transformation methods.

Step 170: triggering the expression of Gam, Exo, and Beta proteins of the λ-red recombinase expression plasmid by adding arabinose.

Step 180: co-transforming the crRNA expression plasmid and the linear DNA into the first transformant to obtain a second transformant. The co-transforming step can be performed by electroporation or other conventional transformation methods.

Step 190: incubating the second transformant in which the Cas9 expression plasmid expresses a tracrRNA and a Cas9 protein, and the crRNA expression plasmid expresses a crRNA. The tracrRNA, the Cas9 protein and the crRNA cooperatively form a Cas9 protein complex to produce a double-stranded break specific to the first specific sequence of the second transformant. The homologous recombination region and the second specific sequence of the second transformant undergo homologous recombination to insert the donor DNA into the first specific sequence of the second transformant.

The genome editing method according to the present disclosure further includes a recovery step, in which the second transformant is cultured in an antibiotic-free medium for 2 to 3 hours.

Moreover, the genome editing method according to the present disclosure further includes a screening process, in which the second transformant is cultured in a medium containing a first antibiotics after the recovery process. The first antibiotics is preferably tetracycline.

4. Experimental Conditions of Genome Editing Method

In order to obtain a high efficiency and a high fidelity integration of large DNA into the specified target site, the superior recovery condition of the present disclosure was verified.

4-A. The Cas9 Expression Plasmid of the Present Disclosure (pCas9') and the Conventional Cas9 Expression Plasmid The construction of the pCas9' refers to previous descriptions and FIG. 1. The conventional Cas9 expression plasmid pCas9 is commercially available from Addgene (Plasmid #42876). The λ-red recombinase expression plasmid is exemplarily pKD46 (commercially available). The crRNA expression plasmid is exemplarily pCRISPR::LacZ, and the length of the linear DNA is exemplarily 1.4 kb.

pCas9 and pKD46 were co-transformed into *E. coli* MG1655 strain by electroporation to produce the first transformant of the control group. pCas9' and pKD46 were co-transformed into *E. coli* MG1655 strain to produce the first transformant of the pCas9' group, followed by adding arabinose to trigger the expression of Gam, Exo and Beta proteins of pKD46. pCRISPR::LacZ and the linear DNA were co-transformed into the first transformant of the control group to obtain the second transformant. In addition, pCRISPR::LacZ and the linear DNA were co-transformed into the first transformant of the pCas9' group to obtain the second transformant. The second transformants of the control group and the pCas9' group were cultured in the S.O.C. medium (New England Biolab™, antibiotics-free) at 37□, then plated onto the Km/Tc/IPTG/X-gal plate for 20-24 h at 37□. The blue and while colonies on the agar plate were photographed and counted using Automatic Colony Counter (SK-Electronics, Kyoto city, Japan). It is worth noting that the white colonies represent the successful genetic recombination due to the insertion of the linear DNA to block LacZ gene expression. The colony forming units (cfu) were calculated by multiplying the average colony number by the dilution fold. All quantitative data were analyzed by student's t-test using a two-tailed distribution. The data represent the average values of at least three independent experiments. $P<0.05$ was considered significant.

Figure 3:
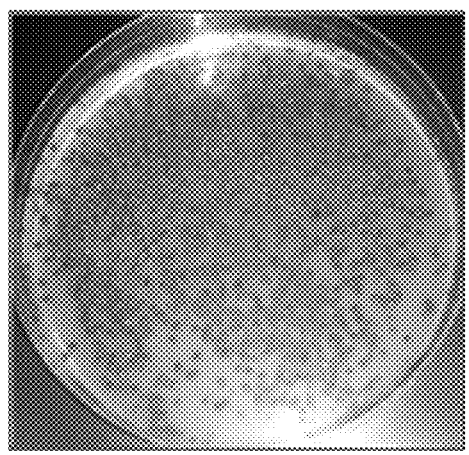
FIG. 3 shows a colony formation according to the genome editing method of the present disclosure compared with the conventional method.
Figure 3:
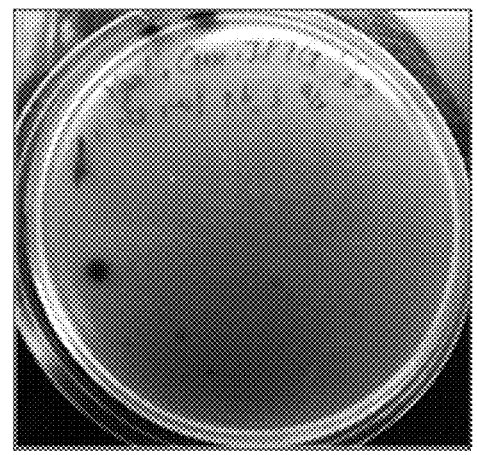

The colony formation of the pCas9 group and the pCas9' group is shown in FIG. 3. The LacZ gene would be disrupted and cells grew into white colonies if cells underwent DSB and survived by virtue of SOS response. As shown in FIG. 3, the ratio of the white/blue colonies of the pCas9 group is smaller than that of the pCas9' group, indicating the elevated accuracy of the transformation by the modified pCas9' plasmid of the present disclosure.

4-B. Recovery Conditions

According to the genome editing method of the present disclosure, *E. coli* suffers a certain level of stress during the transformation. Moreover, bacterial chromosome cleavage by CRISPR/Cas9 during the recovery process causes irreversible damages for bacterium. In order to elevate transformation efficiencies of the genome editing method of the present disclosure, the recovery time for the second transformant in the recovery process is increased from standard 1 hour to 2-3 hours. Further, the volume of the recovery medium SOC is increased from conventional 1 ml to 2 ml, which allows *E. coli* to recover DNA breakages by undergoing homologous recombination in a better environment.

For the optimal incubation time, pCas9' and pKD46 were co-transformed into *E. coli* to obtain the first transformant, followed by adding arabinose to trigger the expression of Gam, Exo and Beta proteins of pKD46. pCRISPR::LacZ and a linear DNA (with a 5.4 kb linear DNA) were co-transformed into the first transformant to obtain the second transformant by electroporation. The second transformant was respectively cultured in the S.O.C. medium (New England Biolab™, antibiotics-free) at 37° C. for 1 hour and for 2.5 hours, then plated onto the Km/Tc/IPTG/X-gal plate for 20-24 h at 37° C. to verify by blue-white screening process.

For the optimal incubation volume, pCas9' and pKD46 were co-transformed into E. coli to obtain the first transformant, followed by adding arabinose to trigger the expression of Gam, Exo and Beta proteins of pKD46. pCRISPR::LacZ and a linear DNA (with a 3.9 kb linear DNA) were co-transformed into the first transformant to obtain the second transformant by electroporation. The second transformant was respectively cultured in 1 ml S.O.C. medium and 2 ml S.O.C. medium (New England Biolab™, antibiotics-free) at 37° C. for 2.5 hours, then plated onto the Km/Tc/IPTG/X-gal plate for 20-24 h at 37° C. to verify by blue-white screening process.

Figure 4A:
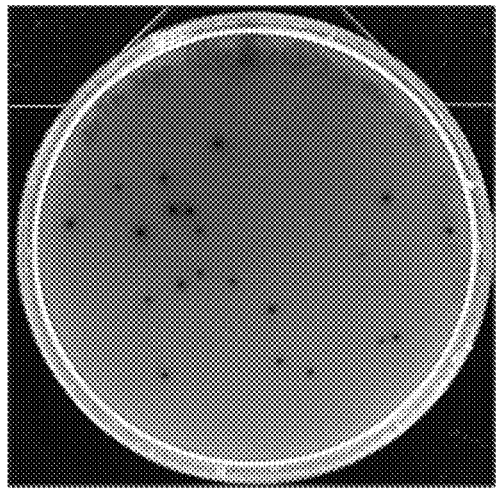
FIG. 4A and FIG. 4B show colony formations under different recovery conditions according to the genome editing method of the present disclosure.
Figure 4A:
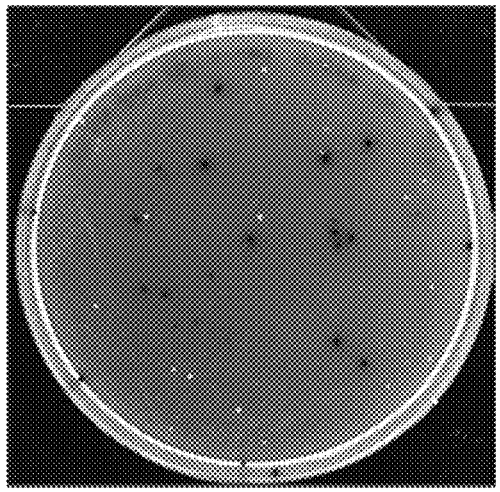
Figure 4B:
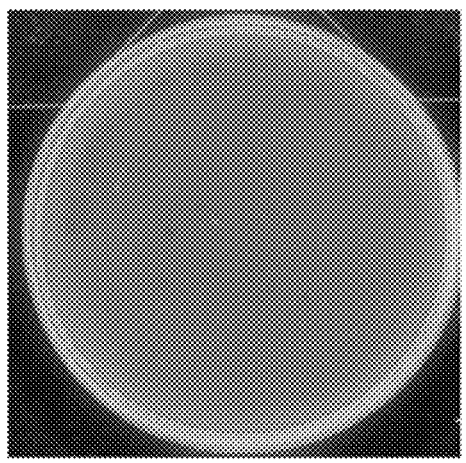
Figure 4B:
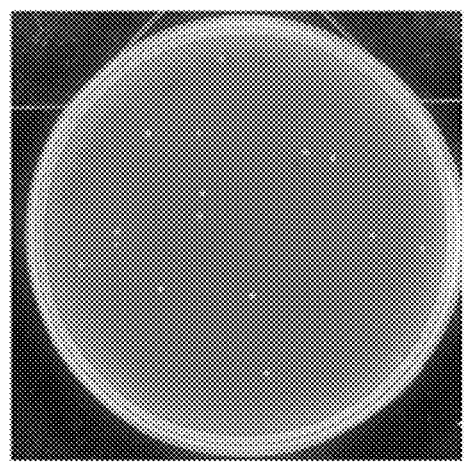

Referring to FIG. 4A, the colony forming units (cfu) of white colonies for the 1 hour incubation group is smaller than that of the 2.5 hours incubation group (17 white colonies for 2.5 hours incubation, and 0 white colonies for 1 hour incubation). FIG. 4B shows that the colony forming units (cfu) of white colonies in 2 ml S.O.C medium incubation group (20 white colonies) is larger than that of white colonies in 1 ml S.O.C medium incubation group (0 white colonies). FIG. 4A and FIG. 4B collectively prove that the optimal recovery condition plays a role in bacterial damaging repair and cell survival after CRISPR/Cas9-mediated DNA cleavage.

4-C. Linear DNA Preparing

In order for linear DNA to have high quality for the subsequent electroporation, the purified DNA undergoes dialysis by a membrane filter (MF-Millipore Membrane Filter, #VSWP02500, pore size: 0.025 μm) to remove impurities in solution, thereby elevating the ratio of 260/230 to about 2. In addition, the time constant of electroporation can be increased to over 5.5 ms.

For the verification of the optimal linear DNA preparation, pCas9' and pKD46 were co-transformed into E. coli to obtain the first transformant, followed by adding arabinose to trigger the expression of Gam, Exo and Beta proteins of pKD46. A dialytic linear DNA and a non-dialytic linear DNA (both containing a 10 kb linear DNA) were respectively co-transformed with pCRISPR::LacZ into the first transformant to obtain the second transformant by electroporation. The second transformant was cultured in S.O.C. medium (New England Biolab™, antibiotics-free) at 37° C. for 2.5 hours, then plated onto the Km/Tc/IPTG/X-gal plate for 20-24 h at 37° C. to verify by blue-white screening process.

Figure 5:
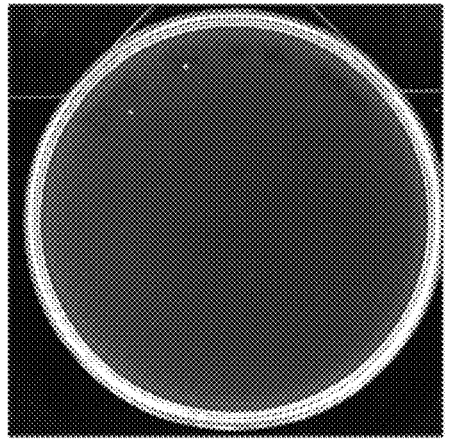
FIG. 5 shows colony formations under different linear DNA preparations according to the genome editing method of the present disclosure.
Figure 5:
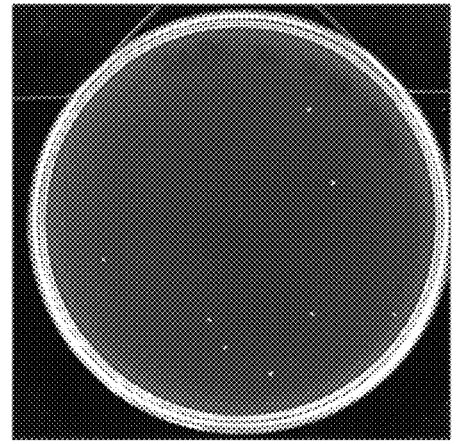

FIG. 5 shows the verification results that the colony forming units (cfu) of white colonies in the dialysis group (8 white colonies) is larger than that of white colonies in the non-dialysis group (2 white colonies), indicating that the recombination efficiency of E. coli can be increased through DNA dialysis in the linear DNA preparation.

5. First Experimental Example—DNA Insertion

Figure 6A:
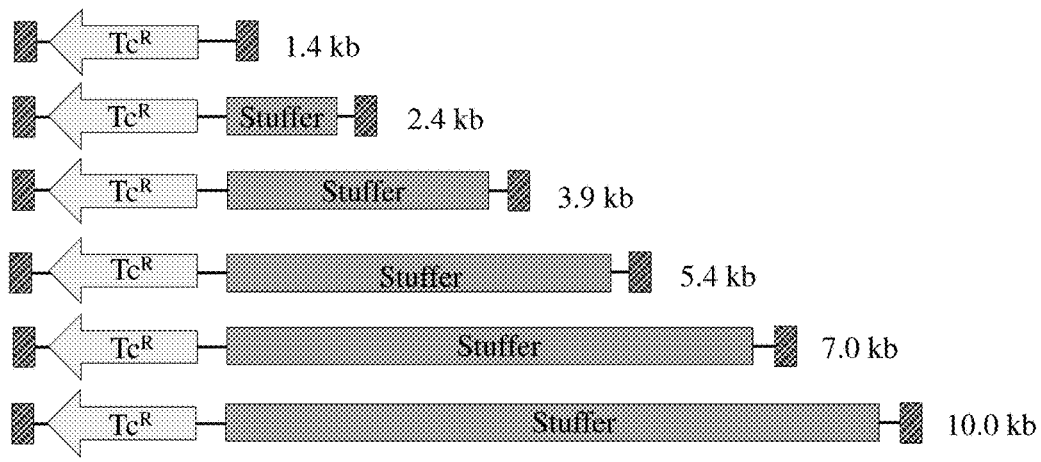
FIG. 6A is a schematic illustration of different sizes of linear DNA.

To evaluate the recombination efficiency for the large size linear DNA by CRISPR/Cas9-mediated integration according to the present disclosure, linear DNA of different sizes (harboring different sizes 1.4, 2.4, 3.9, 5.4, 7.0 and 10 kb of linear DNA) were prepared by PCR (as shown in FIG. 6A). Furthermore, a 1.5 kb region near the 5' end of lacZ gene for recombination was selected so that the left homology arm (HRL) was homologous to the upstream region of lacZ (−53 to −3 bp), while the other (HRR) was homologous to intergenic region of lacZ (1,516-1,566 bp). The primer pairs for each size of linear DNA are referred to Table 1.

According to the embodiment of the present disclosure, the E. coli strain is an MG1655 strain (Food Industrial Development Institute, Hsinchu city, Taiwan), which is a lineage of the common K-12 strain in biological studies. All E. coli strains were routinely cultured in LB medium. The λ-red recombinase expression plasmid was pKD46 (commercially available), and the crRNA expression plasmid was pCRISPR::LacZ.

Figure 6B:
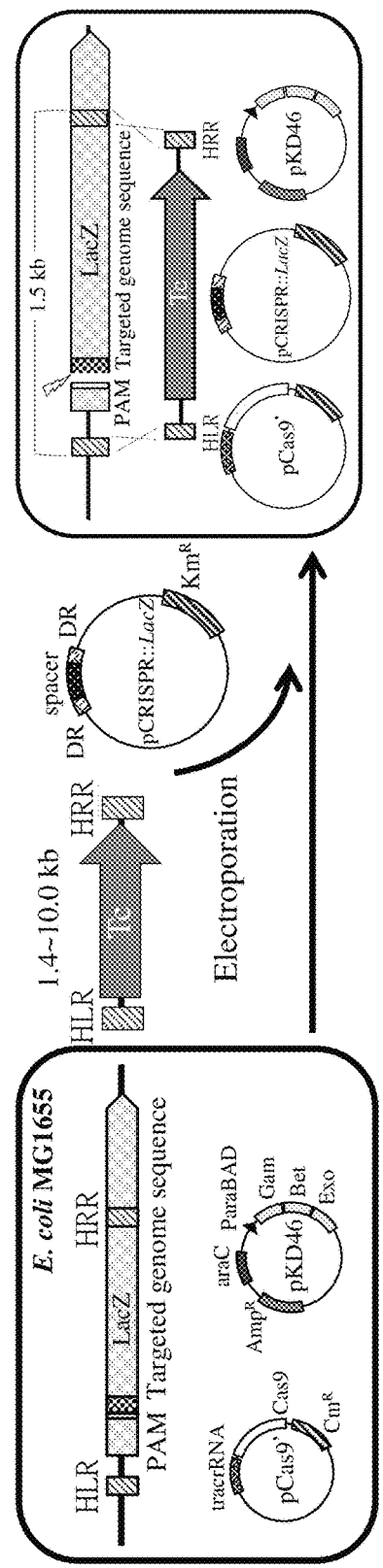
FIG. 6B is a schematic illustration of double-stranded break induction and homologous recombination according to the present disclosure.

FIG. 6B is a schematic illustration of double-stranded break induction and homologous recombination according to the present disclosure. To evaluate the size limit of CRISPR/Cas9-mediated integration, we constructed plasmids harboring cassettes that comprised the $Tc^R$, donor DNA of different lengths, and flanking HR (right and left, each 50 nt), then prepared linear DNA of different sizes (1.4, 2.4, 3.9, 5.4, 7.0 and 10 kb) by PCR (FIG. 6A). pCas9' and pKD46 were co-transformed into the wt MG1655 to form a first transformant, followed by triggering the expression of Gam, Exo and Beta proteins of pKD46 via arabinose, so as to stabilize the subsequent linear DNA integration. The linear DNA amplicons were co-electroporated with pCRISPR::LacZ into the MG1655 harboring pCas9' and pKD46 to obtain a second transformant for an experimental group (as in FIG. 6B). Then, the homologous recombination of E. coli occurs through the CRISPR/Cas9 system to cleavage at the specific restriction site of the lacZ gene, thereby inserting the exogenous linear DNA into the lacZ gene. In parallel, the donor DNA was electroporated into the wt MG1655 harboring merely pKD46 as a control transformant. After incubating at 37° C. for 2.5 hours, the second transformant and the control transformant were plated onto the Km/Tc/IPTG/X-gal plate for 20-24 h at 37° C. to verify by blue-white screening process.

The colony forming units (cfu) were calculated by multiplying the average colony number by the dilution fold. In the blue/white screening assay, blue colonies represent that the failure linear DNA integration into bacterium, which causes unsuccessful recombination. On the contrary, white colonies represent the integration of the linear DNA into the bacterial genome and the successful recombination. The recombination rate can be determined by the equation: number of white colonies/total number of white colonies (white colonies and blue colonies)*100%.

Figure 7A:
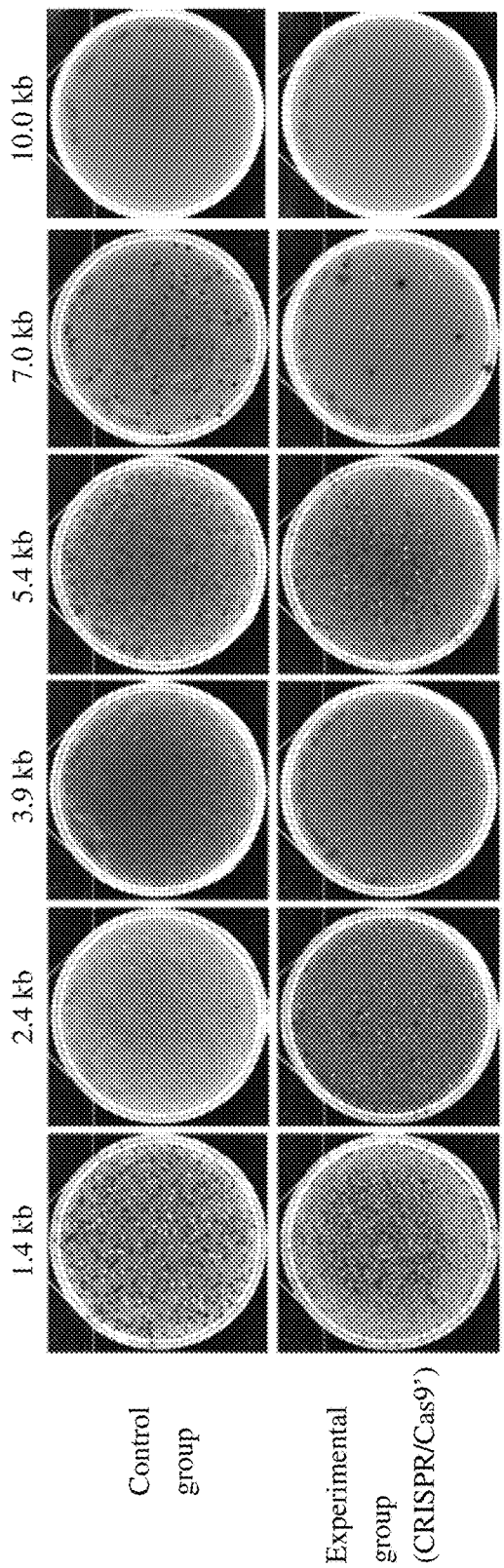
FIG. 7A shows the colony formations after DNA integration for different sizes into bacterial genome according to the present disclosure.

FIG. 7A shows the colony formations after DNA integration for different sizes into bacterial genome according to the present disclosure. The experimental results show that, in the control groups of 1.4, 2.4, 3.9, 5.4, 7.0, and 10 kb, average numbers of the white colonies respectively are 223, 37, 3, 2, 0 and 0. In the experimental groups of 1.4, 2.4, 3.9, 5.4, 7.0 and 10 kb, average numbers of the white colonies respectively are 781, 480, 105, 68, 8 and 5. The average numbers of the white colonies are significantly increased (p<0.05) in all experimental groups compared to control groups regardless of the insertion lengths of linear DNA, which indicates that the homologous recombination of the E. coli can be effectively promoted by using the CRISPR/Cas9 system to specifically cut the target site of lacZ gene in E. coli, thereby improving the genetic recombination rate. Furthermore, in the control groups, once the linear DNA has a size larger than 3.9 kb, the number of white colonies is dramatically reduced to below three. The result indicates that the linear DNA integration in E. coli by the conventional λ-red recombination system is less efficient when the length thereof is larger than 3.9 kb.

Figure 7B:
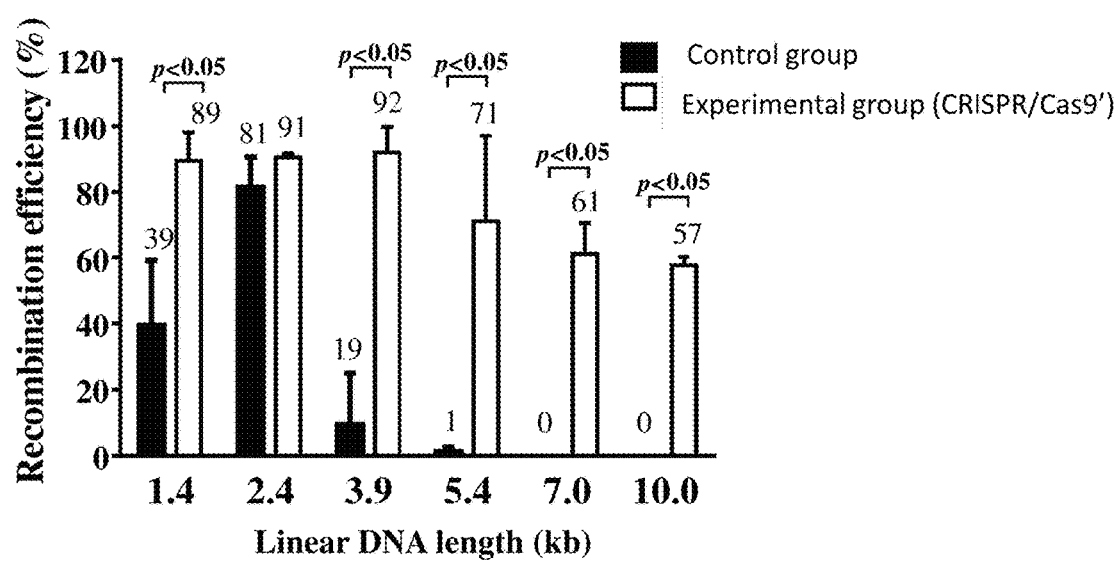
FIG. 7B is a statistics diagram of the recombination efficiency of DNA integration for different sizes into bacterial genome according to the present disclosure.

FIG. 7B is a statistics diagram of the recombination efficiency of DNA integration for different sizes into bacterial genome according to the present disclosure. In the control groups, the successful recombination rate for 1.4 and 2.4 kb DNA integration are respectively 39% and 91%, and the group of 3.9 kb is dropped to 19%. Further, when the linear DNA has a size larger than 3.9 kb, the success rate of picking the recombined colonies is significantly reduced to below 1%. However, in the experimental groups, the rates of the groups of 1.4, 2.4, and 3.9 kb are all 90%, and the rate of groups of 5.4, 7.0 and 10 kb are respectively 71, 61 and 57%. The comparison between the control group and the experimental group indicates that the recombination frequencies for the experimental group are much higher than those of the control group (e.g. from <1% to at least 57% in 3.9 kb DNA integration). These data collectively confirmed that the CRISPR/Cas9 system allowed for efficient integration of DNA as large as 10 kb and bestows a more efficient recombination than the recombineering control at all DNA lengths.

Figure 8A:
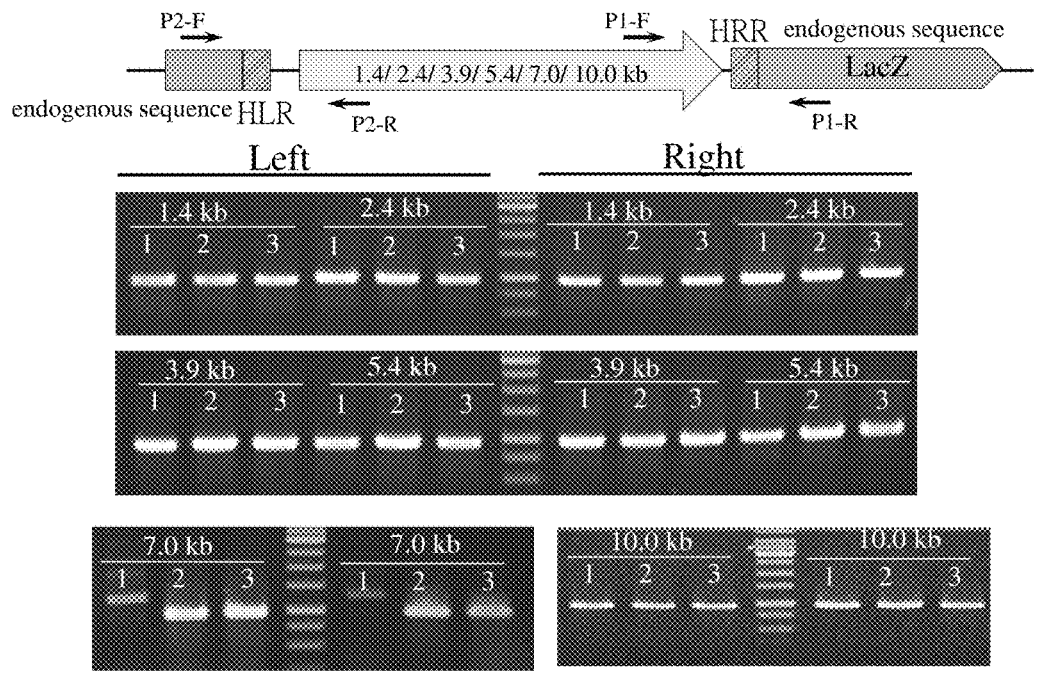
FIG. 8A and FIG. 8B show PCR analyses of the linear DNA of different lengths into the target locus using specific primer pairs according to the present disclosure.

In order to further confirm that the linear DNA has been inserted into the right location of the chromosome, two sets of primers were designed in the experimental group, and 3 to 5 white colonies were randomly picked to conduct colony PCR for the linear DNA inserted into left and right gaps of the chromosome. If the exogenous linear DNA has been inserted into the right location, a PCR signal of 1 kb will be generated. FIG. 8A shows that all the correct sizes of amplicons from the colony for each length of the entire linear DNA were successfully integrated into the chromosome.

Figure 8B:
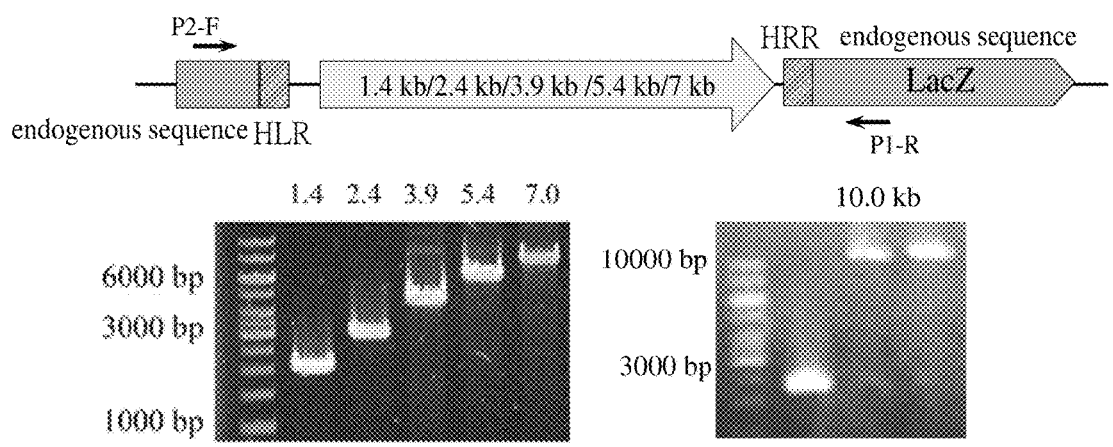

Further, to verify the integration of the entire linear DNA in the CRISPR/Cas9 experimental group, 10 white colonies from each group were picked and colony PCR was performed using primers P1-forward (P1-F) and P2-reverse (P2-R). FIG. 8B confirms the correct size of amplicons from the colony for each length, indicating successful integration of the entire linear DNA into the chromosome, even at 10 kb. The above results confirm that, in the experimental groups, all of the exogenous linear DNA with different sizes were correctly inserted into the lacZ site on the chromosome of *E. coli*.

6. Second Experimental Example—DNA Point Mutation

To test whether the CRISPR/Cas9-mediated genome editing method according to the present disclosure can produce point mutations in *E. coli*, linear DNA harboring point mutations were prepared by PCR. According to the embodiment of the present disclosure, the *E. coli* strain is a WΔ5 strain, which is derived from a W strain (Food Industrial Development Institute, Hsinchu city, Taiwan) by deleting adhE, ldhA, mdh, pflB and arcA genes. All *E. coli* strains were routinely cultured in LB medium. The λ-red recombinase expression plasmid was pKD46 (commercially available), and the crRNA expression plasmid was pCRISPR::gltA. The linear DNA used in the point mutation assay is shown as SEQ ID NO: 9, of which 40 bp of each of the two ends are complementary to the two flanking sequences of the target site on the chromosome of *E. coli*, and the nucleotides at −41 bp to −43 bp are point mutations.

Figure 9A:
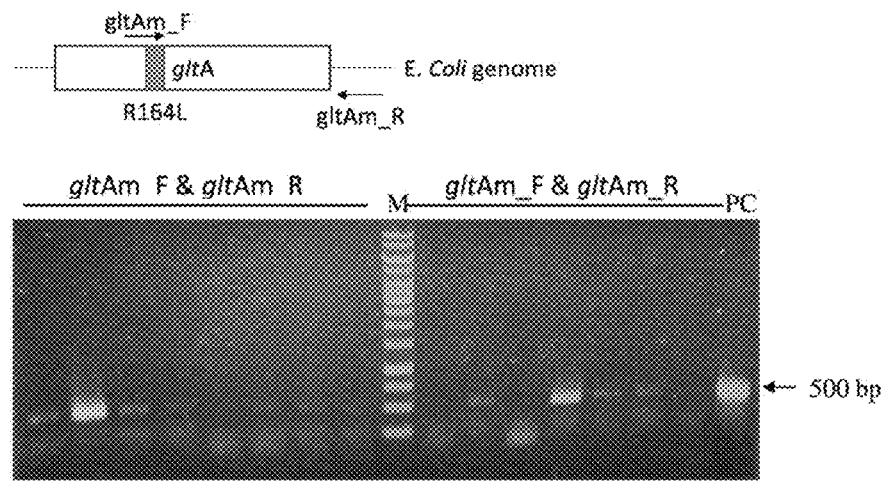
FIG. 9A shows a PCR analysis of the linear DNA with point mutation integrated into the target locus using specific primer pairs according to the present disclosure.

Firstly, pCas9' and pKD46 were co-transformed into a WΔ5 strain of *E. coli* to form a first transformant, followed by triggering the expression of Gam, Exo and Beta proteins of pKD46 via arabinose to produce a first transformant. The linear DNA amplicons were co-electroporated with pCRISPR::gltA into the WΔ5 strain to obtain a second transformant for an experimental group. Then, the homologous recombination of *E. coli* occurs by the cleavage through the CRISPR/Cas9 system at the target site of the gltA gene, thereby inserting the exogenous linear DNA into the gltA gene to obtain a mutant strain-WΔ5#1. After recovering at 37° C. for 2.5 hours, the second transformant was incubated onto plate for 20-24 h at 37° C. In order to further confirm that the linear DNA has been inserted into the right location of the chromosome, two sets of primers that are complementary to the sequences outside the blunt ends of the ligation site on the chromosome were designed for the experimental group (gltAm_F and gltAm_R), numbers of white colonies were randomly picked to conduct colony PCR for the linear DNA inserted into the chromosome. If the exogenous linear DNA has been inserted into the right location, a PCR signal of 500 bp will be generated (FIG. 9A). FIG. 9A shows a PCR analysis of the linear DNA with point mutation integrated into the target locus using specific primer pairs according to the present disclosure.

Figure 9B:
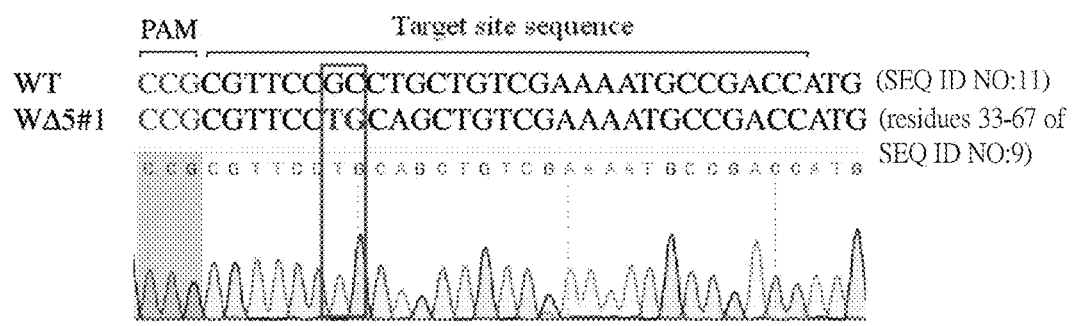
FIG. 9B shows a sequencing analysis of the linear DNA with point mutation integrated into the target locus using specific primer pairs according to the present disclosure.

Further, to reconfirm the integration of linear DNA with point mutation in the CRISPR/Cas9 experimental group, Sanger DNA sequencing was performed. FIG. 9B shows a sequencing analysis of the linear DNA with point mutation integrated into the target locus using specific primer pairs according to the present disclosure, indicating the successful integration of the linear DNA with point mutations into the chromosome (in FIG. 9B, "WT" shows the sequence of SEQ ID NO: 11 and "WΔ5#1" shows the residues 33-67 of SEQ ID NO: 9). The above results confirm that, in the experimental groups, integration of the exogenous linear DNA can produce point mutations specific to the gltA gene of the WΔ5#1 strain of *E. coli* to generate genome-wide editing effects.

7. Third Experimental Example—DNA Replacement

To verify whether the CRISPR/Cas9-mediated genome editing method according to the present disclosure can be applied to gene replacement of heterogeneous genes in *E. coli*, linear DNA harboring heterogeneous genes was prepared by PCR. Exemplarily, linear DNA harboring a heterogeneous lpdA gene was prepared to verify the recombination rate via the CRISPR/Cas9-mediated genome editing method according to the present disclosure. According to the embodiment of the present disclosure, the *E. coli* strain is a W Δ5#1 strain which is obtained from the second experimental example and harbors point mutations. All *E. coli* strains were routinely cultured in LB medium. The λ-red recombinase expression plasmid was pKD46 (commercially available), and the crRNA expression plasmid is pCRISPR::lpdA. The linear DNA used in the point mutation assay is shown as SEQ ID NO: 10, of which 50 bp of each of the two ends are complementary to the two flanking sequence of the target site on the chromosome of *E. coli*, and has a heterogeneous lpdA gene and $Tc^R$.

Firstly, pCas9' and pKD46 were co-transformed into the WΔ5#1 strain of *E. coli* to form a first transformant, followed by arabinose induction. The linear DNA amplicons were co-electroporated with pCRISPR::lpdA into the WΔ5#1 strain to obtain a second transformant. Then, the homologous recombination of *E. coli* occurs by the cleavage through the CRISPR/Cas9 system at the target site of the lpdA gene to generate a mutant strain. The second transformant was recovered at 37° C. for 2.5 hours and incubated onto Km/Tc agar plates for 20-24 h at 37° C. In order to further confirm that the linear DNA has been inserted into the right location of the chromosome, two sets of primers that are complementary to the sequences outside the blunt ends of the ligation site on the chromosome were designed, and numbers of white colonies were randomly picked to conduct colony PCR for the linear DNA inserted into the chromosome. If the exogenous linear DNA has been inserted into the right location, a PCR signal of 3.3 kb will be generated.

Figure 10:
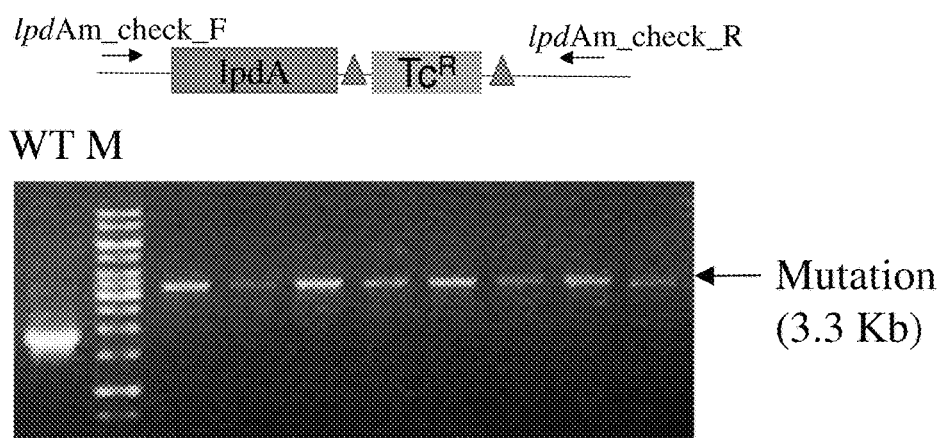
FIG. 10 shows a PCR analysis of the heterogeneous linear DNA replacement of the target locus using specific primer pairs according to the present disclosure.

FIG. 10 shows a PCR analysis of the heterologous linear DNA replacement of the target locus using specific primer pairs according to the present disclosure. As shown in FIG. 10, the picked white colonies harboring the correct PCR products indicates the successful DNA replacement of the heterologous gene into the chromosome of E. coli. The above results confirm that integration of the exogenous linear DNA can produce DNA replacement for the heterologous gene of the WΔ5#1 strain of E. coli to generate genome-wide editing effects.

In summary, by the genome editing method for bacterial of the embodiment in this present disclosure, the scarless integration of dsDNA in different E. coli strains and genetic recombination in bacterium can be successfully conducted. Furthermore, the methodology of the present disclosure facilitates high fidelity integration of dsDNA as large as 10 kb into E. coli chromosome with an efficiency exceeding 57%, thus significantly ameliorating the editing efficiency and overcoming the size limit of integration, replacement and site specific deletion by the genome editing method of the present disclosure. In comparison with conventional technical means using CRISPR/Cas9 for E. coli engineering, the present disclosure achieves more efficient homologous recombination of large DNA fragments using shorter homology arms (40-80 bp) in different E. coli strains by changing the plasmid design and experimental conditions. Therefore, the method of the present disclosure simplifies the procedures of introducing synthetic metabolic pathway into bacterium, so as to allow replacement, integration and site-specific mutations of large DNA segments for genome-wide editing. In the future, the genome editing method according to the present disclosure can be used for regulating bacterial metabolic pathways to achieve desired purposes of producing biomass products, and holds promise in strain optimization, metabolic engineering, and synthetic biology.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present invention delineated by the following claims.

What is claimed is:

1. A Cas9 expression plasmid, comprising a nucleotide sequence of SEQ ID NO: 1 including a tracrRNA sequence, a Cas9 gene sequence and a chloramphenicol resistance gene ($Cm^R$) sequence.

2. A genome editing system for *Escherichia coli* (*E. coli*), comprising:
   an *E. coli* strain;
   a Cas9 expression plasmid according to claim 1;
   a λ-red recombinase expression plasmid including a $P_{araB}$ promoter, a Gam gene, a Bet gene and an Exo gene sequentially;
   a crRNA expression plasmid including a promoter sequence, a crRNA sequence and a spacer sequence, wherein the spacer sequence is complementary to a first specific sequence on a chromosome of the *E. coli* strain; and
   a linear DNA including a right homology arm (HRR), a donor DNA and a left homology arm (HRL), wherein the right homology arm (HRR) and the left homology arm (HRL) cooperatively form a homologous recombination region of which the sequence is complementary to a second specific sequence on the chromosome of the *E. coli* strain.

3. The genome editing system for *E. coli* according to claim 2, wherein the crRNA expression plasmid further includes a tracrRNA sequence, and the tracrRNA sequence and the spacer sequence cooperatively form a single guide RNA (sgRNA) sequence.

4. The genome editing system for *E. coli* according to claim 2, wherein the size of the right homology arm is the same as that of the left homology arm and is between 40 bp and 80 bp.

5. The genome editing system for *E. coli* according to claim 2, wherein the linear DNA further includes a first antibiotic resistant gene.

6. The genome editing system for *E. coli* according to claim 5, wherein the first antibiotic resistant gene is tetracycline resistance gene ($Tc^R$).

7. The genome editing system for *E. coli* according to claim 2, wherein the *E. coli* strain is selected from K-12 strain and W strain.

8. The genome editing system for *E. coli* according to claim 7, wherein the *E. coli* strain is selected from MG1655, WΔ5 and WΔ5#1 strains.

9. A genome editing method for *Escherichia coli*, comprising steps of:
   providing an *E. coli* strain;
   constructing a Cas9 expression plasmid having a nucleotide sequence of SEQ ID NO: 1, wherein the Cas9 expression plasmid includes a tracrRNA sequence, Cas9 gene sequence and a chloramphenicol resistance gene ($Cm^R$) sequence;
   constructing a λ-red recombinase expression plasmid sequentially harboring a $P_{araB}$ promoter, a Gam gene, a Bet gene and an Exo gene;
   constructing a crRNA expression plasmid harboring a promoter sequence, a crRNA sequence and a spacer sequence, wherein the spacer sequence is complementary to a first specific sequence on a chromosome of the *E. coli* strain;
   preparing a linear DNA including a right homology arm (HRR), a donor DNA and a left homology arm (HRL), the right homology arm and the left homology arm cooperatively forming a homologous recombination region of which the sequence is complementary to a second specific sequence on the chromosome of the *E. coli* strain;
   co-transforming the Cas9 expression plasmid and the λ-red recombinase expression plasmid into the *E. coli* strain to produce a first transformant;
   triggering the expression of Gam, Exo, and Beta proteins of the λ-red recombinase expression plasmid by adding arabinose;
   co-transforming the crRNA expression plasmid and the linear DNA into the first transformant to obtain a second transformant; and
   incubating the second transformat, wherein the Cas9 expression plasmid expresses a tracrRNA and a Cas9 protein, the crRNA expression plasmid expresses a crRNA; the tracrRNA, the Cas9 protein and the crRNA cooperatively form a Cas9 protein complex to produce a double-stranded break specific to the first specific sequence of the second transformant; then, the homologous recombination region and the second specific sequence of the second transformant undergo homologous recombination to insert the donor DNA into the first specific sequence of the second transformant.

10. The genome editing method for *E. coli* according to claim 9, wherein the crRNA expression plasmid further includes a tracrRNA sequence, and the tracrRNA sequence and the spacer sequence cooperatively form a single guide RNA (sgRNA) sequence.

11. The genome editing method for *E. coli* according to claim 9, wherein the linear DNA further includes a first antibiotic resistant gene.

12. The genome editing method for *E. coli* according to claim 11, further includes a recovery step, wherein the second transformant is cultured in an antibiotic-free medium for 2 to 3 hours.

13. The genome editing method for *E. coli* according to claim 12, further includes a screening step, wherein the second transformant is cultured in a medium containing a first antibiotics after the recovery step.

14. The genome editing method for *E. coli* according to claim 13, wherein the first antibiotics is tetracycline.

15. The genome editing method for *E. coli* according to claim 9, wherein the step of preparing the linear DNA further includes:

provided a template plasmid;

performing PCR-amplification of the template plasmid by a primer pair to obtain a PCR product, wherein the primer pair is composed of a forward primer and a reverse primer, the 5'-end of the forward primer has a sequence of the left homology arm and the 5'-end of the reverse primer has a sequence that is complementary to the right homology arm;

purifying the PCR product to obtain a DNA solution; and eluting the DNA solution to obtain the linear DNA.

16. The genome editing method for *E. coli* according to claim 15, wherein the DNA solution is eluted through a membrane filter with a pore size of 0.025 µm.

\* \* \* \* \*